United States Patent [19]
Semertzides

[11] Patent Number: 5,601,579
[45] Date of Patent: Feb. 11, 1997

[54] METHOD FOR THE TREATMENT OF BOWEL ADHESIONS

[75] Inventor: John N. Semertzides, Cincinnati, Ohio

[73] Assignee: Medex, Inc., Dublin, Ohio

[21] Appl. No.: 365,774

[22] Filed: Dec. 29, 1994

[51] Int. Cl.$^6$ ................................................. A61B 17/04
[52] U.S. Cl. ......................................................... 606/151
[58] Field of Search ............................. 128/898; 606/151

[56] References Cited

U.S. PATENT DOCUMENTS

| | | | |
|---|---|---|---|
| 4,840,626 | 6/1989 | Linsky et al. | 604/364 |
| 5,002,551 | 3/1991 | Linsky et al. | 623/11 |
| 5,007,916 | 4/1991 | Linsky et al. | 606/151 |

OTHER PUBLICATIONS

Shimanuki, T. et al "Localized prevention of postsurgical adhesion formation and reformation with oxidized regenerated cellulose", J. Biomed. Mater. Res. 1987 Feb. 21 (2):173–85.

John P. Welch, M.D., *Small and Large Bowel*, Chapter 6—"Adhesions", pp. 154–165 (W. B. Saunders, 1990).

"Approaches to Assessing Host Resistance," by S. Gaylen Bradley and Page S. Morahan, Environmental Health Perspectives, vol. 43, pp. 61–69, 1982.

"Differences in Phagocytosis and Killing by Alveolar Macrophages from Humans, Rabbits, Rats, and Hamsters," by Bach–Yen T. Nguyen, Phillip K. Peterson, Henri A. Verbrugh, Paul G. Quie, and John R. Hoidal, Infection and Immunity, vol. 36, No. 2, May 1992, pp. 504–509.

"Nonoxidative Fungicidal Mechanisms of Mammalian Granulocytes: Demonstration of Components with Candidacidal Activity in Human, Rabbit, and Guinea Pig Leukocytes," by Robert I. Lehrer, Kathryn M. Ladra, and Randall B. Hake, Infection and Immunity, vol. II, No. 6, Jun. 1975, pp. 1226–1234.

"Effects of Human and Rabbit Serum on Viability, Permeability, and Envelope Lipids and Serratia marcescens," by Susan Beckerdite–Quagliata, Michael Simberkoff, and Peter Eisbach, Infection and Immunity, vol. 11, No. 4, Apr. 1975, pp. 758–766.

"Altered Motility and Duration of Bacterial Overgrowth in Experimental Blind Loop Syndrome," by P. G. Justus, MD, L. E. McHerron, BA, and T. T. Ward, MD, Digestive Diseases and Sciences, vol. 29, No. 7, Jul. 1984, pp. 643–648.

"The Microflora of the Obstructed Bowel," by Peter A. Sykes, Kenneth H. Boulter, and Philip F. Schofield, Br. J. Surg., vol. 63 (1976) pp. 721–725.

"Sclerosing Encapsulating Peritonitis in Four Dogs and a Cat," by Elizabeth M. Hardie, DVM, PhD, Diplomate ACVS, James B. Rottman, DVM, Diplomate ACVP, and Julie K. Levy, DVM, The College of Veterinary Medicine, NC State Univ., Raleigh, NC, Veterinary Surgery 23:107–114, 1994.

"Experimental Models for Quantitative Studies on Adhesion Formation in Rats and Rabbits," by Lena Holmdahl, M. Al–Jabreen, and B. Risberg, Dept. of Surgery, Ostra Hospital, Univ. of Goteborg, Sweden, Eur. Surg. Res. 1994;26:248–256.

"Peritoneal Adhesion Formation," by J. B. Bridges, F. R. Johnson, and H. W. Whitting, Depts. of Anatomy, Queen's Univ., Belfast, Northern Ireland; London Hospital Medical College, London, England; and Emory Univ., Atlanta, Georgia, Acta anat. 61:203–212 (1965).

(List continued on next page.)

*Primary Examiner*—Gary Jackson
*Attorney, Agent, or Firm*—Wood, Herron & Evans, P.L.L.

[57] ABSTRACT

A method for treating bowel adhesions 20, 22, 24, 26 with an adhesion barrier 56 in the form of a flexible strip 76 of material is provided. The bowel 12, 14 is surgically accessed to expose the affected bowel portions 11, 13, 15, 17 and then the flexible strip 76 of material comprising the adhesion barrier 56 is applied to the bowel surfaces 50, 52, 54, 60, 62 of those portions 11, 13, 15, 17.

23 Claims, 2 Drawing Sheets

OTHER PUBLICATIONS

"Role of Mast Cells in Peritoneal Adhesion Formation," by Shael M. Liebman, MD, Jacob C. Langer, MD, Jean S. Marshall, PhD, and Stephen M. Collins, MD, PhD., The American Journal of Surgery, vol. 165, Jan. 1993 pp. 127–130.

"The Peritoneum, Retroperitoneum, and Mesentery Abnormal Contents of the Peritoneal Cavity," by K. V. F. Jubb, Peter C. Kennedy, and Nigel Palmer, Pathology of Domestic Animals, 3rd Ed., vol. 2, 1985, pp. 333–338.

"Some Species Differences in Fibrinolysis and Blood Coagulation," by R. G. Mason and M. S. Read, J. Biomed. Mater. Res., vol. 5, pp. 121–128 (1971).

"Fibrinolytic Activity in Serosal and Synovial Membranes," by Olaf Myhre–Jensen, MD; Sigrid Bergmann Larsen; and Tage Astrup, PhD, Arch Path, vol. 88, Dec. 1969, pp. 623–630.

METHOD FOR THE TREATMENT OF BOWEL ADHESIONS

FIELD OF THE INVENTION

This invention relates generally to the bowel and more particularly, to a method of treating adhesions of the bowel.

BACKGROUND OF THE INVENTION

Many people suffer from severe abdominal pain created by the formation of adhesions. An adhesion is the abnormal union of separate tissue surfaces that often occurs during the healing process of injured cells, tissues and organs. Adhesions may result after any trauma sustained by the body such as a surgery or a wound.

Adhesions are indiscriminate as they may form on organs ranging in diversity from the heart to the female reproductive organs. The formation of adhesions creates serious medical problems because they often interfere with the proper functioning of an organ and may result in the total loss of function in that organ.

To date, the successful treatment of adhesions varies from organ to organ. While one form of adhesion treatment may work well on a specific organ, it may not work at all on another organ because organs differ in various ways such as in size, shape, function, and chemical composition.

One form of treatment consists of the application of an absorbable adhesion barrier made of oxidized regenerated cellulose. This adhesion barrier and a method of preventing adhesions by the use of this barrier are disclosed in U.S. Pat. Nos. 5,002,551 and 5,007,916 ('551 and '916 patents). The disclosed adhesion barrier is a sterile knitted fabric prepared by the controlled oxidation of regenerated cellulose. The barrier is made available in 3"×4" single layer pieces. Typically a dry piece of the adhesion barrier is laid upon the surface of an injured organ or upon tissue surrounding the injured organ whereupon it turns into a gel within one to two days. The gel adheres to the surface of the injured organ or surrounding tissue via ionic bonds. This prevents the injured surface area from directly contacting nearby tissue while healing, thereby reducing adhesion formation between the organ and nearby tissue.

The gel also regulates proper protein concentration and prevents fibrin deposition at the injured organ surface during the healing process, thereby eliminating thick scar tissue that could form and cause adhesions. After about four to six weeks the gel is naturally absorbed by macrophages of the body. By this time, the injured surface has partially or completely healed without forming adhesions by growing a layer of epithelium over the injured organ surface beneath the adhesion barrier gel.

The adhesion barrier disclosed in the '551 and '916 patents is used to reduce adhesion formation in gynecologic pelvic surgery. The viability of this adhesion barrier in gynecologic pelvic surgery is due to a number of factors. In comparison with various other organs, gynecological organs, such as the uterus and ovaries, are quite small and symmetrical in shape. It is therefore fairly simple to place one or a couple small pieces of this barrier on these organs to adequately cover them or to place the barrier on the pelvic sidewall to treat the affected area of the organ.

Another factor adding to the successful use of this adhesion barrier in gynecologic pelvic surgery is that gynecological organs do not move significantly or alter their shape during normal functioning. Thus, a piece of the adhesion barrier can simply be laid upon the organ without the risk of becoming displaced by movement during normal functioning of the organ. Furthermore, the barrier adheres succinctly to these organs because the surface area of such organs is fairly dry, especially since these organs are not fluid filled. Fluid filled organs, on the other hand, diffuse fluid through the organ wall when injured. Thus, the surface area of these fluid filled organs are moist and it was thought, would cause the adhesion barrier to float off of the organ, hindering the treatment and prevention of adhesions.

The success of adhesion barrier treatment is greatly reduced by the presence of an infection in the organ. The body will perceive the infection and possibly the barrier as foreign and quickly consume the barrier along with the infection. The presence of virulent bacteria in the organ creates greater chances of infection and the resulting consumption of the barrier. The barrier may even serve as an energy source for the infection and bacteria. Gynecological organs do not normally house such virulent bacteria. This is one reason that adhesion barriers have been successfully used on gynecological organs.

Of all the types of adhesions, adhesions of the bowel involve some of the most serious problems. Since the small intestine alone has an average adult length of 9 feet in a healthy person, adhesions can be numerous as loops of the small intestine are in constant contact with each other creating an environment conducive to the formation of adhesions. Another source of adhesion formation is between the peritoneum and intestines, as the intestines are completely encased by the peritoneum. These adhesions create severe abdominal pain and interfere with the digestive process, which can be life threatening.

A number of procedures have been used for treating adhesions of the bowel, but all have been unsuccessful. Some of these procedures include ultrasound treatments and other, more complicated, surgical techniques. The known, surgical techniques can be dangerous to the patient by causing additional complications, such as infection. Various medications have also been administered to patients suffering from bowel adhesions. Some medications have resulted in unwanted side effects such as blindness, while other medications have resulted in death due to the medication's high level of toxicity.

Certain characteristics of the bowel make adhesion treatment and prevention difficult. The size of the bowel creates the possibility of numerous adhesions. The small bowel winds back and forth in the abdominal region, thereby being in direct and constant contact with itself and the peritoneum. It is therefore nearly impossible for a specific bowel surface to heal without being in direct contact with itself or the peritoneum. Furthermore, successive waves of involuntary contractions pass along the walls of the intestines during digestion, moving the intestines and further increasing the chance of one area of the intestine coming into contact with surrounding tissue.

To complicate matters, the bowel is a fluid filled organ which is prone to cause infection upon injury as fluid diffuses through the bowel wall. The bowel also contains virulent bacteria which significantly increases the chance of infection. As a result of all of these complicating factors, prior to my invention adhesions of the bowel had yet to be successfully treated in a consistent, predictable fashion.

SUMMARY OF THE INVENTION

Due to the complicating factors inherent with the bowel, the successful application of an adhesion barrier as a form of treatment seemed unlikely. However, the present invention provides a highly effective method for treating adhesions of the bowel and preventing the subsequent formation of adhesions thereon, by using an adhesion barrier, preferably comprised of oxidized regenerated cellulose. To this end and in accordance with the principles of the present invention, a portion of the bowel is surgically accessed and oxidized regenerated cellulose is applied to the bowel surface. The result has been to provide an effective method for treating the bowel by which adhesions are reduced or completely eliminated, thus eliminating the need for multiple surgeries. While some patients have minor adhesion formations, others have severe adhesion formations that are life-threatening. Patients with severe adhesion formations often undergo numerous surgeries in an attempt to treat their condition and relieve their severe pain. By the method of the invention the formation of subsequent substantive adhesions is greatly reduced or eliminated such that any adhesions that reoccur are usually less severe and may not even require surgery. Subsequent adhesions after use of my method are often very weak and cobweb-like, and can be simply brushed away by the surgeon's hand or with a blunt instrument.

In accordance with a further aspect of the present invention, the adhesion barrier is advantageously placed on the bowel surface in only a single layer and further, only on the bowel surface and not on the surrounding peritoneum. By applying the barrier to the surface of only the bowel portion rather than both the bowel and the peritoneum, the results have unexpectedly been better than if both surfaces are covered with the adhesion barrier.

Before placing the barrier on the bowel surface, the bowel surface is desirably washed to remove all undesirable blood or other matter. The washing solution may be ringer's lactate solution. After washing the bowel, but before placing the barrier thereon, a liquid protein may be applied to the bowel surface. This protein prevents leakage of fibrin from the bowel. The liquid protein may be a protein such as thrombin.

After washing the bowel and applying liquid protein, the barrier is placed on the bowel surface and advantageously sutured in place. Suturing is to be accomplished without puncturing into the interior of the bowel to prevent bowel contents from spilling or seeping out. Due to the length of the bowel, the adhesion barrier is preferably applied in an elongate strip. This strip may be formed as one integral strip or by attaching several smaller barrier pieces together.

The bowel may be surgically accessed by incising the abdominal cavity. Generally, an incision is made along a midline of the abdominal cavity. This enables a surgeon to access the bowel located on both sides of the midline with little difficulty.

By virtue of the foregoing there is thus provided a method for treating adhesions of the bowel that is very successful, yet surprisingly quite simple. These and other objects and advantages of the present invention shall be made apparent from the accompanying drawings and description thereof.

BRIEF DESCRIPTION OF THE DRAWINGS

The accompanying drawings, which are incorporated in and constitute a part of the specification, illustrate embodiments of the invention, and together with a general description of the invention given above, and the detailed description given below, serve to explain the principles of the invention.

DETAILED DESCRIPTION OF THE DRAWINGS

Figure 1:
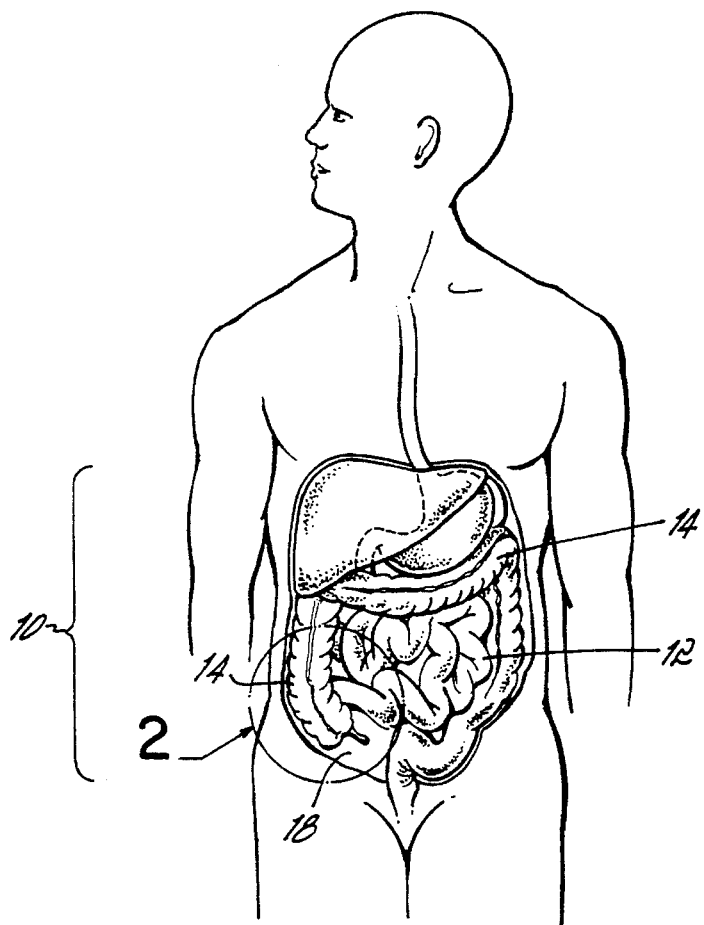
FIG. 1 is a front, internal view of a human peritoneal cavity with the intestines located therein.
Figure 2:
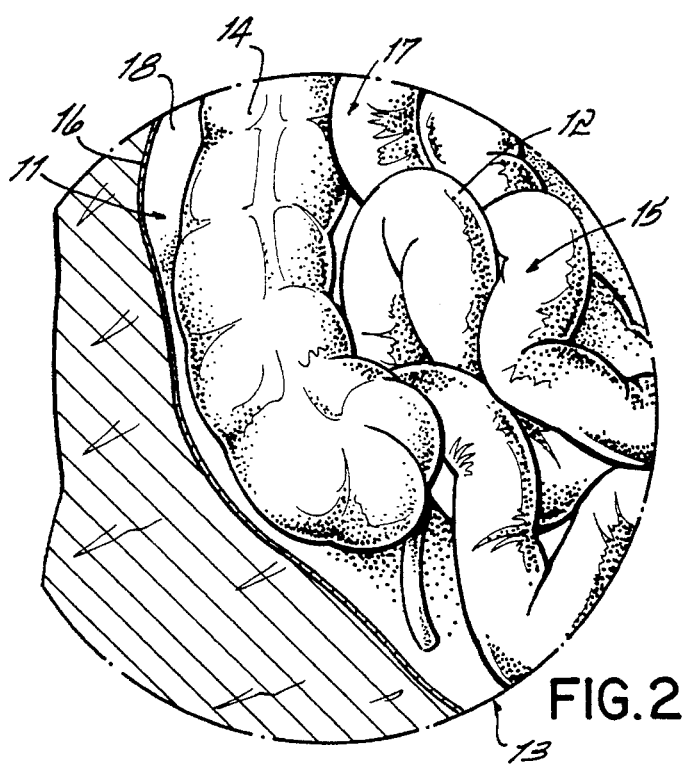
FIG. 2 is an enlarged view of the intestines taken from the encircled portion 2 of FIG. 1.

As shown in FIGS. 1–2, a major portion of a person's internal mid-section 10 is occupied by the small intestines 12 and the large intestines 14, collectively and more generally called the bowel. Both small intestines 12 and large intestines 14 are completely encased by the peritoneum 16 and located within the peritoneal cavity 18.

Small intestines 12 and large intestines 14 have as their outer most layer a single cell-thick lining of squamous mesothelium (not shown), which, lubricated by peritoneal fluid, allows small intestines 12 and large intestines 14 to move freely within cavity 18. Mobility is critical to proper functioning of both intestines 12, 14. During the process of digestion, food is moved along intestines 12, 14 by involuntary waves of contractions, better known as peristalsis. Loss of such mobility results in loss of proper functioning of intestines 12, 14, which in turn, may prove fatal.

Figure 3:
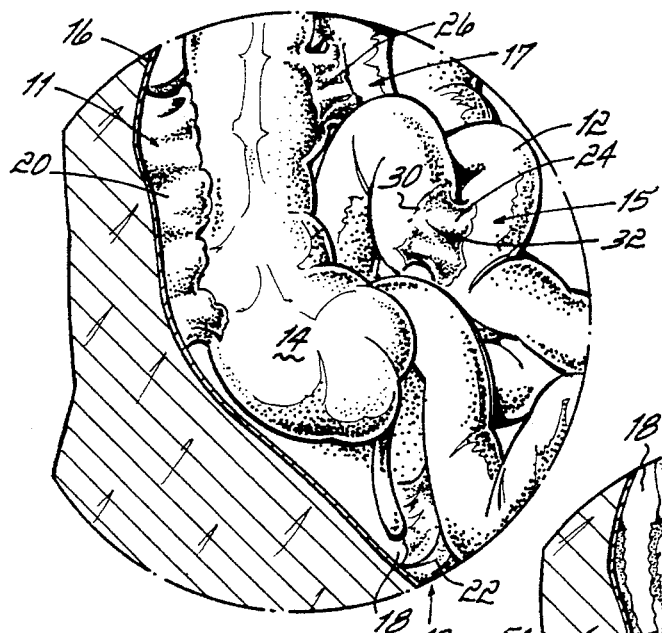
FIG. 3 is an enlarged view of the intestines with various adhesions.

As shown in FIG. 3, loss of mobility may be the result of peritoneal adhesions 20, 22, intraorgan adhesions 24, or interorgan adhesions 26. Peritoneal adhesions 20, 22 form between the peritoneum 16 and intestines 12, 14. Intraorgan adhesions 24 form between opposing surfaces 30, 32 of the same organ, such as small intestines 12. Interorgan adhesions 26 form between adjacent organs, such as small intestines 12 and large intestines 14.

Adhesions 20, 22, 24, 26 may result from trauma sustained by peritoneum 16 or by intestines 12, 14. After such trauma a fibrin-rich inflammatory exudate (not shown) is released into peritoneal cavity 18. Also, after such trauma the ability of peritoneum 16 or intestines 12, 14 to lyse this fibrin is reduced, thus resulting in the formation of fibrinous adhesions 20, 22, 24, 26. Adhesions 20, 22, 24, 26 may organize into permanent adhesions by incorporating collagen. The formation of permanent adhesions is usually accompanied by loss of intestinal mobility and function.

Figure 6A:
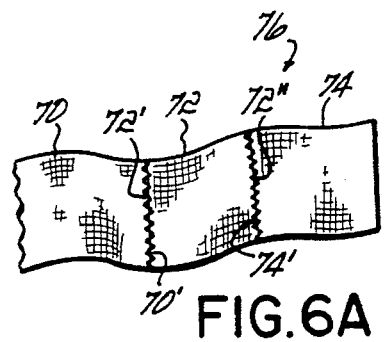
FIG. 6A is a top view of adhesion barrier pieces sutured together.
Figure 6B:
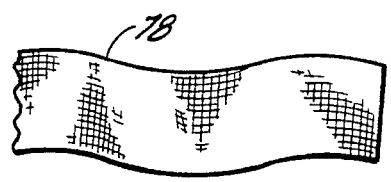
FIG. 6B is a top view of a single elongated strip of adhesion barrier formed as an integral piece of material.
Figure 7:
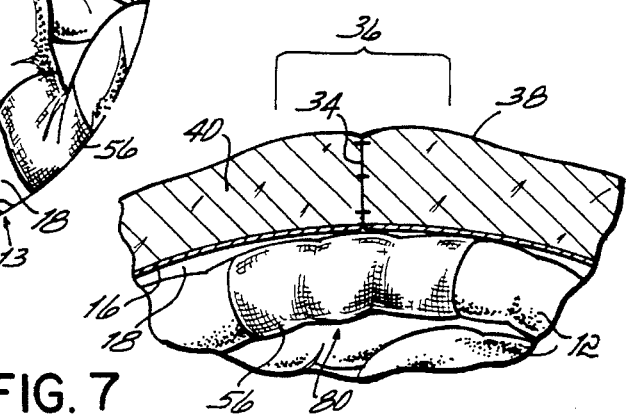
FIG. 7 is a cross-sectional view of a human peritoneal cavity after intestinal surgery for treatment of adhesions.

With reference to FIGS. 4–7, there is shown a method of treating adhesions 20, 22, 24, 26 of intestines 12, 14 in accordance with the principles of the present invention. Intestines 12, 14 must first be surgically accessed to expose at least those portions 11, 13, 15, 17 of intestines 12, 14 affected with adhesions 20, 22, 24, 26. As shown in FIG. 7, an incision 34 located along the mid-line 36 and extending through the skin 38, overlying musculature 40, and peritoneum 16, and into peritoneal cavity 18 may be used to access the affected portions 11, 13, 15, 17 of intestines 12, 14. However, the location and size of incision 34 may vary depending on a number of factors such as the location of adhesions 20, 22, 24, 26 or the location of any previous incisional scars.

Figure 4:
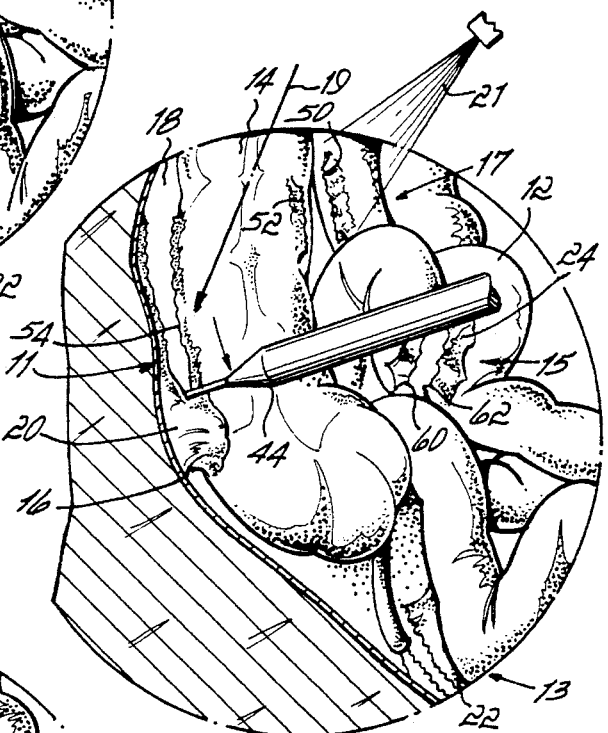
FIG. 4 is an enlarged view of intestinal adhesions being dissected with a dissecting tool.

Once the desired portion 11, 13, 15, and/or 17 of intestines 12, 14 has been exposed via incision 34, intestines 12, 14 are to be freed of one or more adhesions 20, 22, 24, 26. The freeing of intestines 12, 14 can be achieved in various ways such as will be readily appreciated by those skilled in the art. As shown in FIG. 4, one way to free intestines 12, 14 is by dissection with a sharp dissecting tool 44 to completely access the injured intestinal surfaces 50, 52, 54, 60, 62.

After dissecting and accessing the injured intestinal surfaces 50, 52, 54, 60, 62 intestines 12, 14 are desirably washed to remove unwanted blood and other matter (not shown) from peritoneal cavity 18 before placing an adhesion barrier 56 onto intestines 12, 14. The washing solution may be a warm, mildly disinfecting solution such as ringer's lactate solution. Washing can be accomplished by flushing peritoneal cavity 18 with a stream 19 of washing solution.

After washing intestines 12, 14 and removing excess fluids such as by aspiration, a liquid protein may be placed on intestines 12, 14 to prevent any possible leakage of fibrin from intestines 12, 14. Reducing fibrin leakage reduces the likelihood of subsequent adhesion formation. Liquid protein, such as thrombin, may advantageously be sprayed as at 21 onto intestines 12, 14. The injured intestinal surfaces 50, 52, 54, 60, 62 should be completely covered with this protein to achieve the best results.

Figure 5:
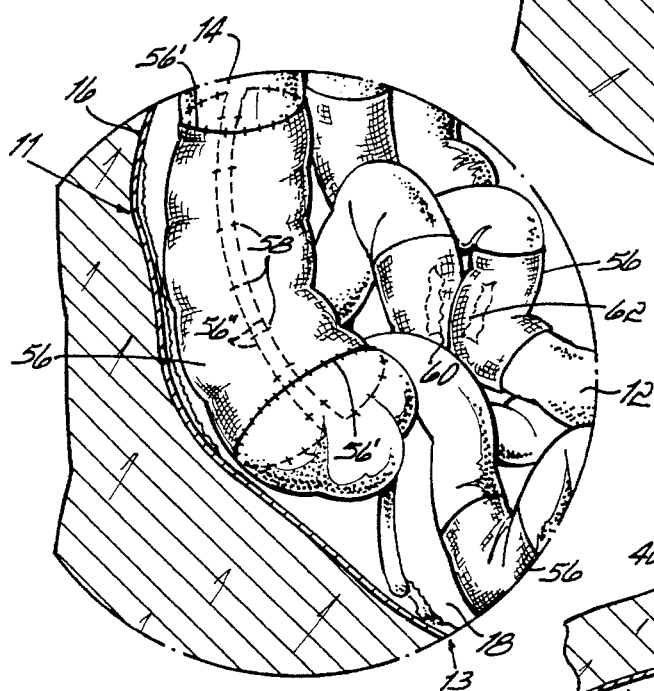
FIG. 5 is an enlarged view of the intestines treated with adhesion barriers.

After washing intestines 12, 14 and spraying intestines 12, 14 with protein, adhesion barrier 56 is placed upon intestines 12, 14 as shown in FIG. 5. Adhesion barrier 56 is advantageously placed on all injured intestinal surfaces 50, 52, 54, 60, 62. Since all injured surfaces 50, 52, 54, 60, 62 are covered, adhesion barrier 56 need not be placed on surrounding peritoneum 16. Adhesions 20, 22, 24, 26 are thereby treated and will be substantively prevented from subsequently forming on all surfaces 50, 52, 54, 60, 62.

Since intestines 12, 14 are fluid filled, barrier 56 may not adhere to intestines 12, 14 sufficiently. Thus, barrier 56 may be sutured 58 to intestines 12, 14. Suturing can be carried out using a 4-0 Vicryl suture. Continuous sutures 58 are advantageously placed along edges 56' 56" of barrier 56 such that sutures 58 are about one centimeter apart.

Suturing is limited to the intestinal wall and is to be achieved without puncturing through the intestinal wall into the interior cavity (not shown) of intestines 12, 14. Any leakage from intestines 12, 14 is undesirable as such leakage creates an environment conducive to the growth of bacteria and subsequent infection. If an infection results at the site of adhesion barrier 56 on intestines 12, 14, the infection itself may consume barrier 56 using it as an energy source. If barrier 56 is consumed and therefore not present on intestines 12, 14, subsequent adhesions will likely form.

Typically, suturing barrier 56 to intestines 12, 14 will maintain barrier 56 on intestines 12, 14 long enough to allow barrier 56 to turn into a gel that will succinctly adhere to intestines 12, 14. Thus, when barrier 56 is sutured to intestines 12, 14, barrier 56 will stay in place until it is naturally consumed by macrophages.

Commercially, adhesion barrier 56 is made available in 3"×4" rectangular pieces 70, 72, 74 as shown in FIG. 6A. Since intestines 12, 14 are quite long, a singular such rectangular piece of barrier 56 will not likely cover affected portion 11, 13, 15, 17 of intestines 12, 14 sufficiently to prevent reoccurrence of adhesions 20, 22, 24, 26. It may therefore be necessary to connect pieces 70, 72, 74 of barrier 56 together to form a longer strip 76 as shown in FIG. 6A. Pieces 70, 72, 74 may be connected by various methods, such as suturing. Pieces 70, 72, 74 of barrier 56 are placed end to end such that adjacent edges 70', 72', 72" and 74' are next to each other. Edges 70', 72' may be sutured together using a 4-0 Vicryl suture. Similarly, edges 72" 74' may be sutured in this same manner. The length of the injured intestinal surface 50, 52, 54 dictates the number of pieces 70, 72, 74 to be sewn together and used thereon. For example, a twelve inch injured surface will require three pieces of barrier 56 to be sewn together to form a strip 76 which is twelve inches long and three inches wide. Once sutured together, strip 76 may then be placed on intestines 12, 14 in the prescribed manner above. Alternatively, a single elongated strip 78 may be formed as an integral piece of material as shown in FIG. 6B.

After adhesion barrier 56 has been placed on intestines 12, 14, incision 34 is closed preferably by suturing. However, before closing incision 34, barrier 56 may be placed on portion 80 of intestines 12 that are located immediately beneath incision 34, as shown in FIG. 7. This reduces the chance of any adhesions forming during the healing process of incision 34. Any adhesions that may form are less severe such that they can easily be brushed away like cobwebs.

In use, there is therefore provided a method for treating adhesions 20, 22, 24, 26 of the bowel 12, 14 by accessing the affected portions 11, 13, 15, 17 of the bowel 12, 14 and applying one or more pieces of adhesion barrier 56 to that portion. A single layer of the barrier 56 needs to be applied only upon affected portions 50, 52, 54, 60, 62 of the bowel 12, 14, but not on surrounding peritoneum 16. Before applying the barrier 56, the bowel 12, 14 is washed 19 and the excess liquid is then removed. A liquid protein may then be applied 21 prior to placing the barrier 56 on the injured bowel surfaces 50, 52, 54, 60, 62 and once the barrier 56 has been placed on the bowel surfaces 50, 52, 54, 60, 62, it is desirably sutured 58 thereto.

By virtue of the foregoing, bowel adhesions are successfully treated with little or no reoccurrence of significant adhesions. Where adhesions subsequently form, they are often easily treated with a second surgery such as by simply wiping away these cobweb-like adhesions. An adhesion barrier can be reapplied to treat these subsequent adhesions if necessary. Some of these subsequent adhesions may not even require surgery at all. In accordance with this invention, patients are thus treated successfully with great results and, in some cases, without the reoccurrence of life-threatening debilitating adhesions. This method of treating the bowel is believed to provide the first instance of controlled healing of the injured bowel within a closed abdomen since sutures and their analogs.

While the present invention has been illustrated by the description of embodiments thereof, and while the embodiments have been described in considerable detail, it is not the intention of Applicant to restrict or in any way limit the scope of the appended claims to such a detail. Additional advantages and modifications will readily appear to those skilled in the art. For example, the entire bowel can be accessed by a midline incision, or just a very small portion can be accessed by other techniques, such as by endoscopic techniques. The invention in its broader aspects is, therefore, not limited to the specific details, representative method, and illustrative examples shown and described. Accordingly, departures may be made from such details without departing from the spirit or scope of Applicant's general inventive concept,

What is claimed is:

1. A method for treating the human bowel with an adhesion barrier in the form of a flexible strip of material, the method comprising the steps of:

surgically accessing a portion of the human bowel having an adhesion; and, applying said flexible strip of material to an outer surface of said bowel portion over the adhesion and which portion of the bowel is free of infection-inducing leakage.

2. The method of claim 1 further comprising forming said barrier from oxidized regenerated cellulose.

3. The method of claim 1 further comprising applying the barrier in only a single layer to the surface of said bowel portion.

4. The method of claim 1 further comprising washing the surface of said bowel portion before applying said barrier.

5. The method of claim 4 wherein said surface is washed with a ringer's lactate solution.

6. The method of claim 1 further comprising applying a liquid protein to the surface of said bowel portion before applying said barrier.

7. The method of claim 6 wherein said protein is thrombin.

8. The method of claim 1 further comprising suturing the barrier to said bowel portion.

9. The method of claim 8 further comprising suturing said barrier without puncturing into the interior of the bowel.

10. The method of claim 8 wherein said incising is performed along a midline of said abdominal cavity.

11. The method of claim 1 wherein said bowel is surgically accessed by incising an abdominal cavity.

12. The method of claim 1 further comprising forming the flexible strip from a plurality of sections of the barrier by placing said sections edge to edge and joining said edges together.

13. The method of claim 12 wherein said edges are joined together by suturing.

14. A method for treating the human bowel with an adhesion barrier in the form of a flexible strip of material, the method comprising the steps of:

surgically accessing a portion of the human bowel having an adhesion;

applying a liquid protein to the surface of the bowel portion;

applying said flexible strip of material to an outer surface of said bowel portion over the adhesion and which portion of the bowel is free of infection-inducing leakage; and suturing said flexible strip of material to said bowel portion.

15. The method of claim 14 further comprising applying the barrier in only a single layer to the surface of said bowel portion.

16. The method of claim 14 further comprising washing the surface of said bowel portion before applying said protein.

17. The method of claim 16 wherein said surface is washed with a ringer's lactate solution.

18. The method of claim 14 wherein said protein is thrombin.

19. The method of claim 14 wherein the suturing step is effected without puncturing into the interior of the bowel.

20. The method of claim 14 wherein said bowel is surgically accessed by incising an abdominal cavity.

21. The method of claim 14 wherein said incising is performed along a midline of said abdominal cavity.

22. The method of claim 14 further comprising forming the flexible strip from a plurality of sections of the barrier by placing said sections edge to edge and joining said edges together.

23. The method of claim 22 wherein said edges are joined together by suturing.

* * * * *

UNITED STATES PATENT AND TRADEMARK OFFICE
CERTIFICATE OF CORRECTION

PATENT NO. : 5,601,579
DATED : February 11, 1997
INVENTOR(S) : Semertzides, John N. (M.D.)

It is certified that error appears in the above-indentified patent and that said Letters Patent is hereby corrected as shown below:

On the face of the Patent, in the first column, delete "[73] Assignee: Medex, Inc." No Assignee is designated for this Patent.

Signed and Sealed this

Thirtieth Day of September, 1997

Attest:

BRUCE LEHMAN

Attesting Officer

Commissioner of Patents and Trademarks